United States Patent [19]
Lowder

[11] Patent Number: 5,951,511
[45] Date of Patent: Sep. 14, 1999

[54] COLON CLEANSING APPARATUS AND METHOD

[76] Inventor: Eldon L. Lowder, 7835 S. 1300 East, Sandy, Utah 84094

[21] Appl. No.: 09/033,330

[22] Filed: Mar. 2, 1998

[51] Int. Cl.$^6$ .............................. A61M 1/06; A47K 3/22
[52] U.S. Cl. ................................. 604/73; 604/322; 4/443
[58] Field of Search .............................. 4/443, 444, 445, 4/446, 447, 448, 343, 420.2, 420.3, 420.4; 604/73, 323, 326, 355, 356, 322

[56] References Cited

U.S. PATENT DOCUMENTS

| | | | |
|---|---|---|---|
| 1,217,692 | 2/1917 | Bookman . | |
| 3,019,447 | 2/1962 | Sluz . | |
| 3,082,432 | 3/1963 | Pearlman . | |
| 3,922,735 | 12/1975 | Kato | 5/91 |
| 4,645,497 | 2/1987 | Lowder | 604/276 |
| 4,677,700 | 7/1987 | Su | 5/90 |
| 5,050,249 | 9/1991 | Takeda et al. | 4/443 |
| 5,214,803 | 6/1993 | Griffen | 53/425 |
| 5,520,888 | 5/1996 | Berndt | 422/186.08 |
| 5,742,961 | 4/1998 | Casperson et al. | 4/615 |
| 5,754,988 | 5/1998 | Presa | 4/443 |
| 5,809,585 | 9/1998 | Farshad | 4/443 |
| 5,809,586 | 9/1998 | Kitamura | 4/443 |

*Primary Examiner*—Wynn Wood Coggins
*Assistant Examiner*—Patricia Bianco
*Attorney, Agent, or Firm*—Mallinckrodt & Mallinckrodt

[57] ABSTRACT

A colon cleansing apparatus and method for use thereof for introduction of water into a person's colon to flush out fecal matter. The apparatus is used with a standard colon irrigation unit having a board on which a user sits and a splash shield which holds a disposable tip for introducing water into a user's rectum and which directs water expelled from the rectum through an opening through the board into a toilet. The apparatus replaces the toilet by supporting the irrigation unit on an elevated table top above a drain basin having a drain opening leading to the sewage pipes. Water from elevated warm and cold water tanks flows through tubes into a main tube attached to the tip with a valve midway along each of the pair to blend the water entering the main tube to a desired temperature. A spray of water directed at the drain opening prevents sewage pipe clogs by breaking up expelled fecal matter. A spray washing system self-cleaning the drain basin during use. A flushing system sends a large volume of water into the drain basin to flush remaining fecal matter from the drain basin and a fan exhausts lingering odors into the sewage pipe. A hand sprayer allows cleaning of the user and the apparatus and an ozone generator provides ozone to add to the water and to a water-filled sterilization chamber to disinfect the main tube following use.

21 Claims, 9 Drawing Sheets

COLON CLEANSING APPARATUS AND METHOD

BACKGROUND OF THE INVENTION

1. Field

The invention is in the field of colon cleansing devices and colonic boards or units used to introduce water into a person's colon through the rectum to flush fecal matter and other undesired matter from the colon.

2. State of the Art

Colon irrigation or cleansing as a form of corrective and preventative medicine is not a new development but rather one which has gained in popularity in recent years with the coming of age of natural remedies and holistic medicine. The colon is said to play a major role in a person's overall health with various sections thereof interactive with and affecting various parts of a person's anatomy. Colon cleansing is used to flush fecal matter, parasites, excess colon mucus and other unwanted matter from the colon so as to improve a person's health. Such cleansing is typically done periodically by users thereof.

The typical way that colon cleansing was done in the past was by positioning ones-self over a toilet and introducing water into the colon by means of a tube having an insertion proctle, speculum, or tip which was inserted into the person's rectum which tube was connected at the opposite end thereof to an elevated container containing water. Such method was messy with typically poor control of the water flow rate with some of the water with fecal matter exiting the rectum typically missing the toilet bowl and flowing onto the floor. Likewise, the tip was predisposed to fall from the rectum due to the generally vertical position of the person. Only a single temperature of water could be used without refilling the container such that introducing cold water after the warm water typically used so as to determine the extent of the water flow into the colon was difficult.

More recently, in an effort to improve on the colon cleansing process colon irrigation boards have been introduced which are typically flat and of such area as to partially support an adult person thereon with an opening over which a box-like shield is disposed to aid in directing the water and fecal matter outflow from the person's rectum into the opening. The board unit is supported at the end having the opening by the toilet and at the opposite end thereof by a box, chair, or the like. A person positions themself on the board in a reclining position with their rectum adjacent the opening therein and introducing water into the colon by means of the insertion tip into the rectum and connected at the other end thereof to an elevated container containing water as done above. In such a reclining position the flow of water into and out of the rectum is more controllable with the water and fecal matter more likely to go into the toilet due to the box-like shield. However, such colon irrigation boards are typically uncomfortable and lack a downhill drainage route for water and fecal matter which inevitably is splashed on the upper surface of the board to drain into the opening.

Such inadequacies led to the development and patenting of a colon irrigation unit similar to a colon irrigation board but with improved draining and splash shielding by the present inventor. This is U.S. Pat. No. 4,645,497 issued to Lowder which discloses a colon irrigation unit which has an opening at one end thereof with an arcuate shield disposed over the opening so as to form a generally vertically oriented opening leading into the toilet. A vertical sidewall extends laterally from each side of the shield and opening to aid in directing water and fecal matter into the opening. The upper surface of the unit slopes inwardly toward the center thereof and from the head end thereof to the opening with an upstanding lip around the perimeter thereof so as to retain and direct water and fecal matter into the opening away from the user. A tube extends through the shield and out through the opening to aid in positioning and retaining the hose and tip which deliver water to the person's rectum. While the colon irrigation unit provides improved fluid retention and direction toward the opening the unit must be used in conjunction with a toilet and be manually cleaned after each use, such that it is not well suited for use with a toilet in a professional setting such as by a doctor wherein multiple persons use it each day.

Even with the improvements in the colon irrigation unit mentioned, the separate elevated container and tubing apparatus used with the colonic irrigation unit is basically the same as has been used for years. A colon irrigation apparatus and method is needed for use by doctors and other professionals which is easily cleanable for consecutive use by multiple persons, has no odor emitted therefrom, with improved sanitation to prevent cross-contamination of users thereof, and which does not rely on the use of a standard toilet.

SUMMARY OF THE INVENTION

In accordance with the invention, a colon cleansing apparatus and method for use thereof for professional, high-volume usage with a colon irrigation unit. The apparatus comprises an elongate elevated table of sufficient length to fully support an adult person thereon which table is supported by adjustable length legs which can be adjusted to level the colon cleansing apparatus such as on an uneven floor. A sloped basin is built into the table top with a supporting horizontal lip around the perimeter thereof to support a colon irrigation unit. A cabinet enclosed on three sides thereof extends upwardly from one end of the table at the deeper end of the sloped basin which cabinet supports a pair of tanks for warm and cold water, an ozone generator, control valves, piping, and tubing all of which are accessible from the rear thereof.

The apparatus has a warm and cold water introduction system wherein water is fed by means of a single main tube to the colon irrigation unit to be introduced through a disposable proctle or tip attached thereto into the rectum and colon of the user. The water comes from a warm and a cold water tank each mounted to the upper portion of the cabinet in an elevated position relative to the table and colon irrigation unit to gravity feed the water through the main tube and tip and to the rectum of the user. Water is introduced into the warm water tank through a tempering valve operatively connected to both hot and cold water supply pipes with flow thereto controlled by means of a standard toilet flush valve. The tempering valve is thermostat controlled and can be set to a desired temperature and automatically blends the hot and cold water to attain the set temperature so as to guarantee scald proof safety to the user which water goes into the warm water tank. Cold water is directly introduced into the cold water tank with the filling thereof controlled by means of a standard toilet flush valve. A pair of manually actuated valves are used to control the flow of water from the warm and cold water tanks into the main tube to the colon irrigation unit for introduction through the tip into the person's colon. Water and fecal matter expelled from the person's rectum is directed into the shielded opening in the colon irrigation unit, into the sloped basin, and out through a drain in the deep end of the basin to a standard sewer pipe.

A pressure spray system is used to assure that the drain and associated plumbing including the sewer pipe do not get clogged by fecal and other matter expelled during the colon cleansing. The system comprises a power nozzle fed by the cold water supply pipe and controlled by a hand actuated valve which power nozzle sprays a high pressure generally horizontal concentrated stream of cold water into the drain of the basin. The opening of the drain is generally vertically oriented and is of a smaller diameter along with a short length of the pipe attached thereto leading to the sewer pipe than the sewer pipes so as to not plug the sewer pipes and easily unclog by hand. The larger pieces of fecal matter are broken up into smaller pieces by the pressure spray so as to pass easily down the sewer pipes. A screen can be placed over the drain at the bottom of the basin to catch all large debris including items which may be of interest to the doctor such as parasites, undigested pills, etc.

An ozone system allows the introduction of ozone into the warm and cold water tanks for equipment sterilization purposes and for therapeutic reasons as prescribed by a doctor and under a doctor's supervision. The system comprises a fan driven ultraviolet ozone generator or other type ozone generator mounted above the warm and cold water tanks which feeds the ozone generated to a four-way hand actuated gang valve. Two of the valves control the flow of ozone bubbled through the warm and cold water tanks so as to sterilize the tanks, valves, and associated tubing. The third and fourth valves control the flow of ozone to the warm water and cold water tubes which connect to the main hose which connects to the tip inserted into the rectum. The main hose can be sterilized after removal of the disposable tip by inserting the end thereof into a water filled sterilization chamber in the cabinet comprising an elongate tube angled downward from horizontal such that ozonated water fed through the hose and into the sterilization chamber sterilizes both the inside and outside of the main tube for next use with a new disposable tip. An overflow pipe leads to an odor trap and into the sewer pipe.

An odor exhausting system is used to remove the odor emitted by the water and fecal matter expelled from the rectum. The system comprises a fan means comprising an electric fan mounted in a fan chamber in the table top under the cabinet which draws air containing unpleasant odors from inside the basin through an inlet positioned above the water level at the shallow end of the basin into the fan chamber and out through the water trap into the sewer pipe. The trap is filled with water during periods of time during which the fan is not used by means of the overflow pipe from the sterilization chamber to the trap below the fan chamber so odors from the sewer line do not back-up into the basin. The fan is operated by means of a manually actuated electrical switch actuated after a manually actuated valve is opened which drains the water from the trap so that air may pass through the trap into the sewer pipe when the fan is on. Upon turning off of the fan the manually actuated valve must be closed to allow the trap to refill with overflow water from the sterilization chamber.

After colon cleansing is completed a hand held sprayer means comprising a hand held sprayer system allows any fecal matter or other matter on the user to be washed into the basin drain along with such matter on the basin or other parts of the cleansing apparatus. The system comprises a hand actuated valved spray head attached to an elongate tube which pulls out from the upper surface of the table and which is connected from the tempering valve through a pressure regulator such that water of a preselected temperature and required pressure can be sprayed from the valved spray head upon hand actuation thereof.

Cleaning of the basin and of the bottom surface of the colon irrigation unit can be done by means of a fan spray washing system which comprises a pair of fan spray nozzles at opposite sides of the basin above the water line intermediate the ends of the basin. Each fan spray nozzle is fed cold water through a tube which is attached to the cold water supply pipe with a manually actuated valve therebetween to control the flow of water with each fan spray nozzle spraying a horizontally wide one hundred eighty degree spray and forty-five degree upwardly directed spray of water onto the walls of the basin and on the bottom surface of the colon irrigation unit while the unit is being used. The use of the fan spray system during colon cleansing also helps control odors while cleaning.

Cleaning of the basin can also be done by means of a flushing system similar to that used in a standard toilet using water in the warm and cold water tanks which has been sterilized with ozone. The system comprises a standard type flush valve disposed in each of the warm and the cold water tanks and a large diameter pipe extending from the bottom of each tank to a respective inlet port on opposite sides of the basin. Upon activation of the flush valve of either or both tanks water enters the upper portion of the basin intermediate the ends thereof through the inlet ports which provide a large volume of water to flush large amounts of fecal matter and other debris down through the drain and into the sewer pipes. The flushing system can be used in conjunction with the fan spray washing system.

THE DRAWINGS

The best mode presently contemplated for carrying out the invention is illustrated in the accompanying drawings, in which.

DETAILED DESCRIPTION OF THE ILLUSTRATED EMBODIMENTS

The colon cleansing apparatus of the invention includes a support structure comprising a table 20 having an top surface 22, side panels 24 and 26, a front end panel 28, a rear end panel 30, and four legs 32, each leg 32 having an threaded upper end 34. Support table 20 may be constructed from wood covered with an appropriate medical grade coating or from metal such as stainless steel or aluminum. A threaded adapter tube 34 is affixed to the ends of the respective side panels 24 and 26 by means appropriate for the material such as adhesives, welding or brazing. Each of legs 32 is connected to one of threaded adapter tubes 35 by means of a threaded coupling 36, and a locknut 38. The effective length of each of legs 32 can be changed by loosening the respective locknut 38 and threading coupling 36 further onto or off of adapter tube 35 and the respective leg 32 relative to coupling 36 and tightening the respective locknut 38 against coupling 36. A basin 40 is built into table top surface 22 which has generally semicircular front wall 42, a larger radius semi-circular rear wall 44, and a bottom wall 46 which downwardly slopes from front wall 42 to rear wall 44 and which has a generally vertically oriented drain 48 at rear wall 44. A peripheral lip 50 extends around basin 40 of sufficient width to support a colon irrigation unit 52.

Figure 1:
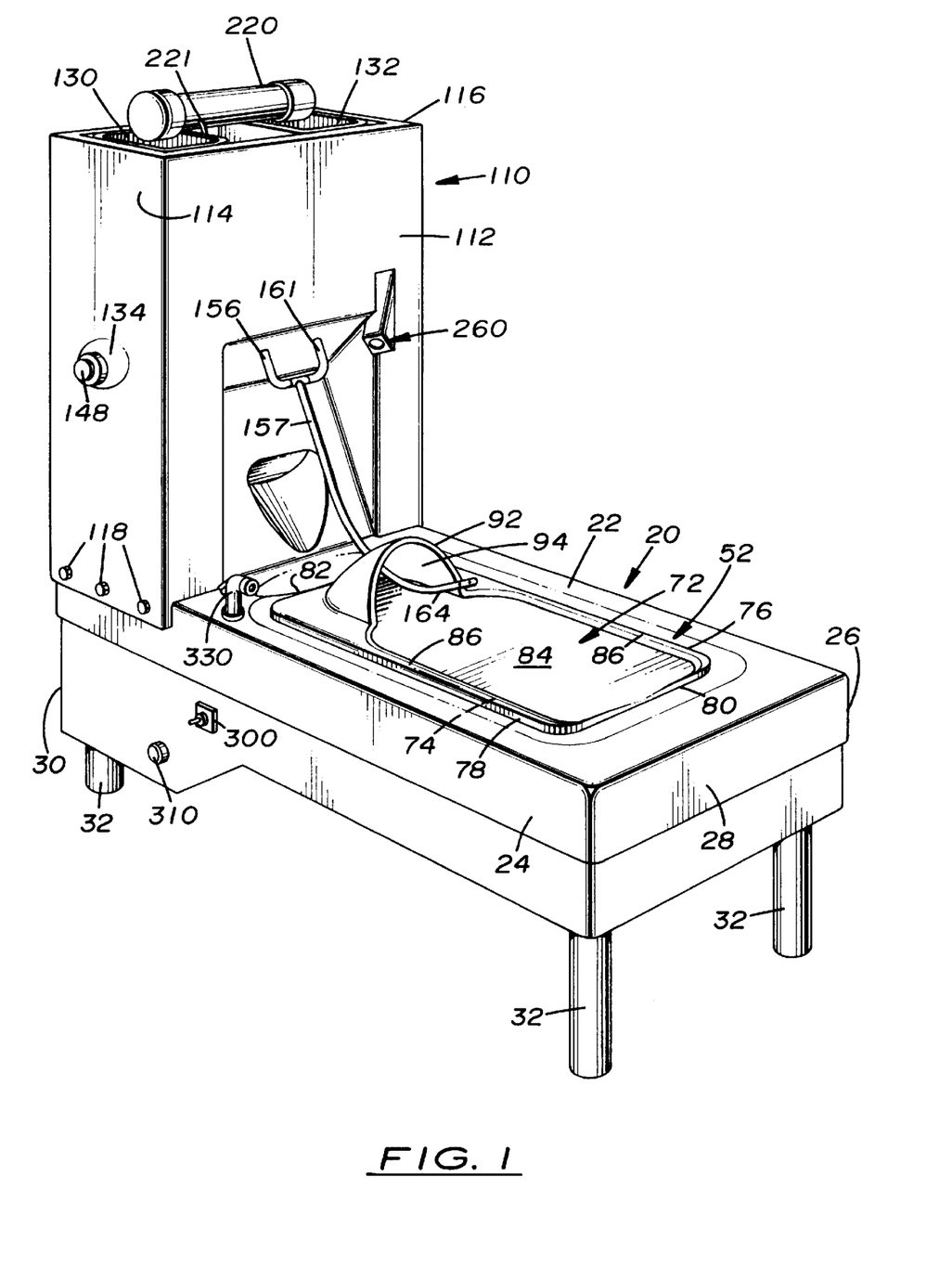
FIG. 1 is a perspective view of the colon cleansing apparatus of the invention with a colon irrigation unit installed thereon.
Figure 1A:
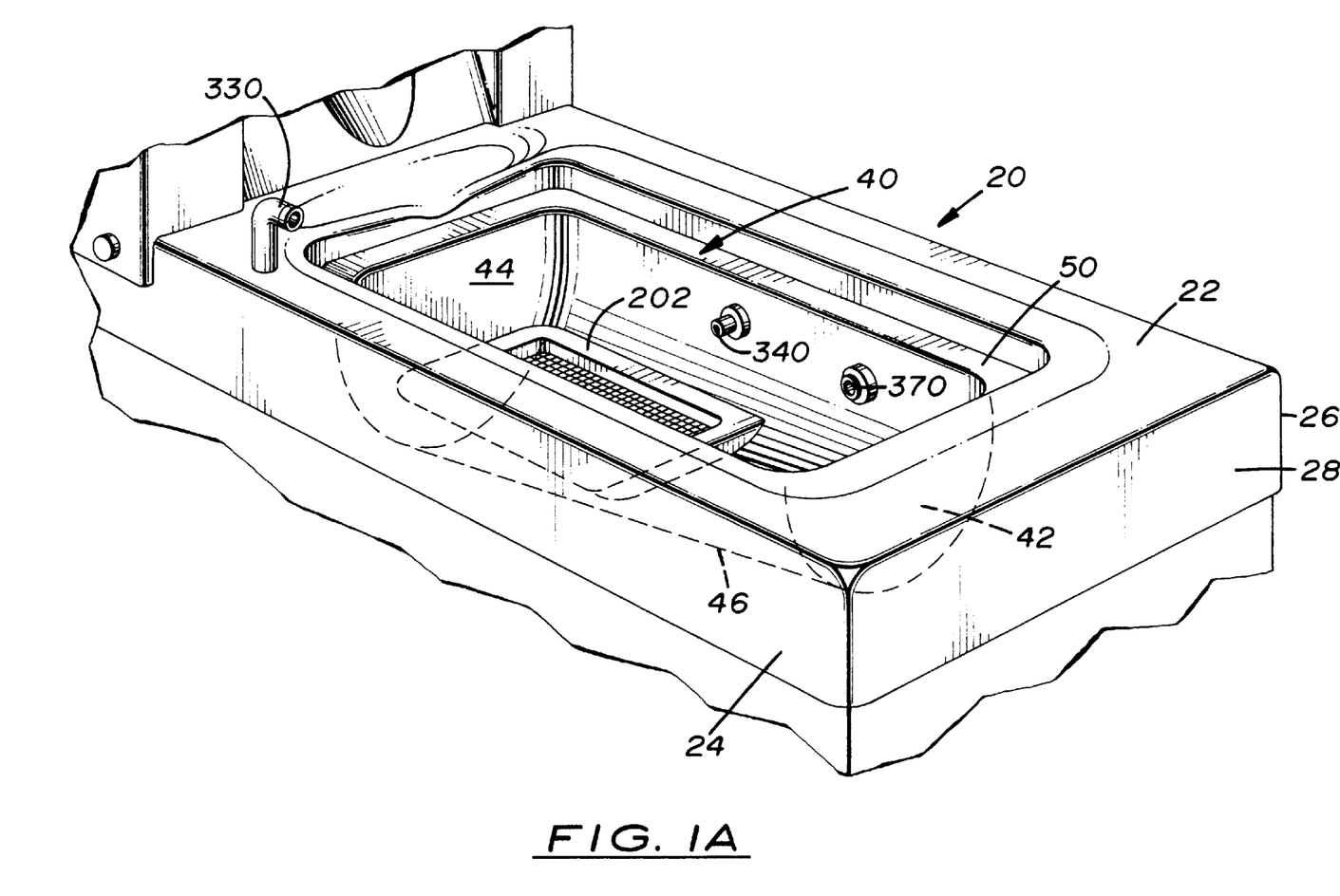
FIG. 1A, a fragmentary perspective view corresponding to FIG. 1 but with the colon irrigation unit removed to show the interior of the basin.

Colon irrigation unit 52 is an elongate structure of the type described in my U.S. Pat. No. 4,645,497 which comprises a top surface 72, a generally flat bottom surface 74, two side walls 76 and 78, a front end wall 80 and a rear end wall 82 connecting top and bottom surfaces 72 and 74. Top surface 72 is generally flat with a depressed portion 84 surrounded by a lip 86. A generally semi-conical shield 92 upwardly extends from top surface 72 defining a generally vertically oriented opening 94 which leads through bottom wall 74 to the basin 40 therebelow. Depressed portion 84 slopes inwardly toward the center thereof and toward opening 94 so as to direct water and fecal matter into opening 94 and away from the user. Basin 40 provides air separation of the user of the colon cleansing apparatus from direct connection with the drainage means and the sewer pipe such that bacteria and other pathogens are less likely to contaminate the user than if there were a solid connection.

Figure 2:
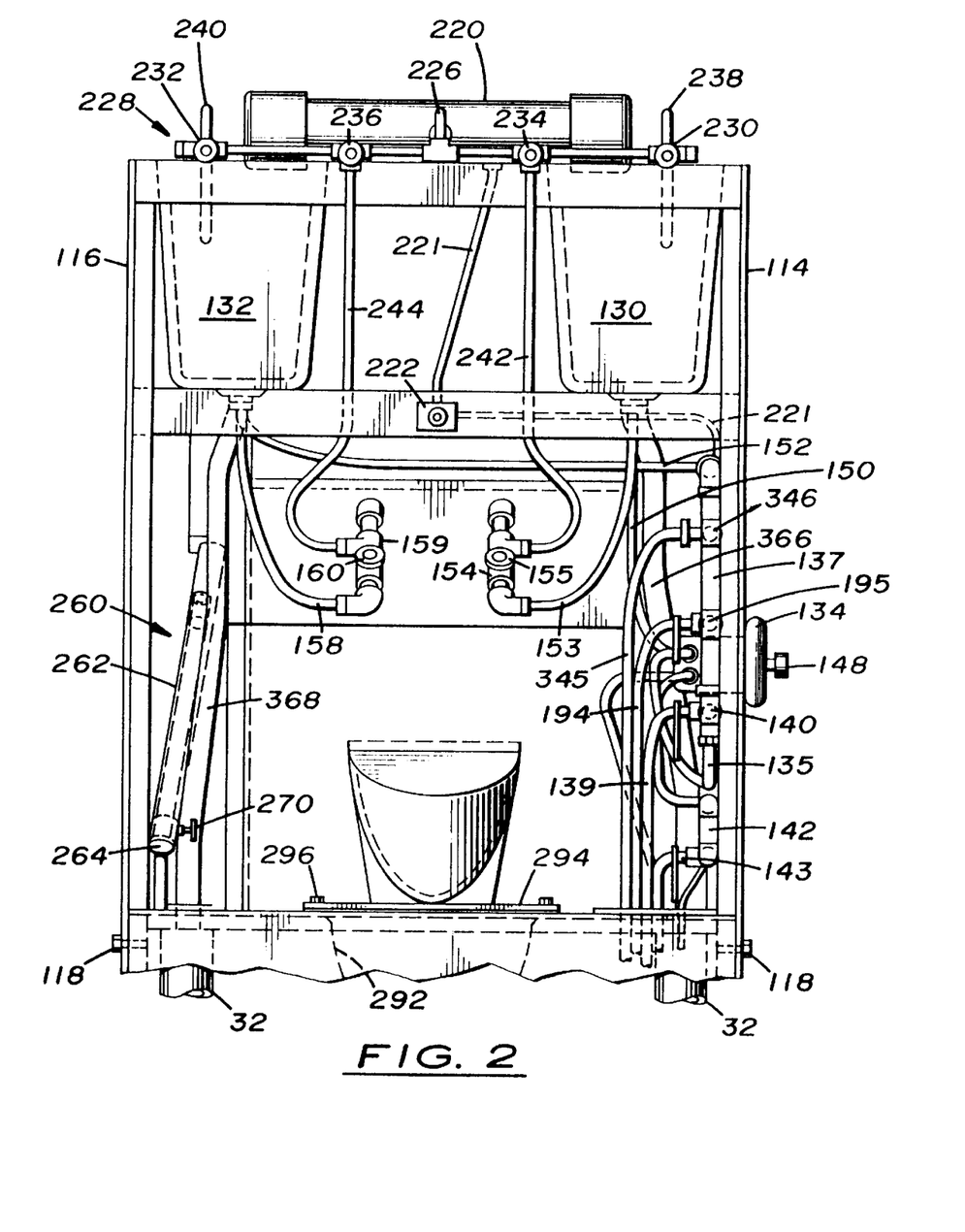
FIG. 2, a rear elevational view taken on the line 2—2 of FIG. 4.
Figure 3:
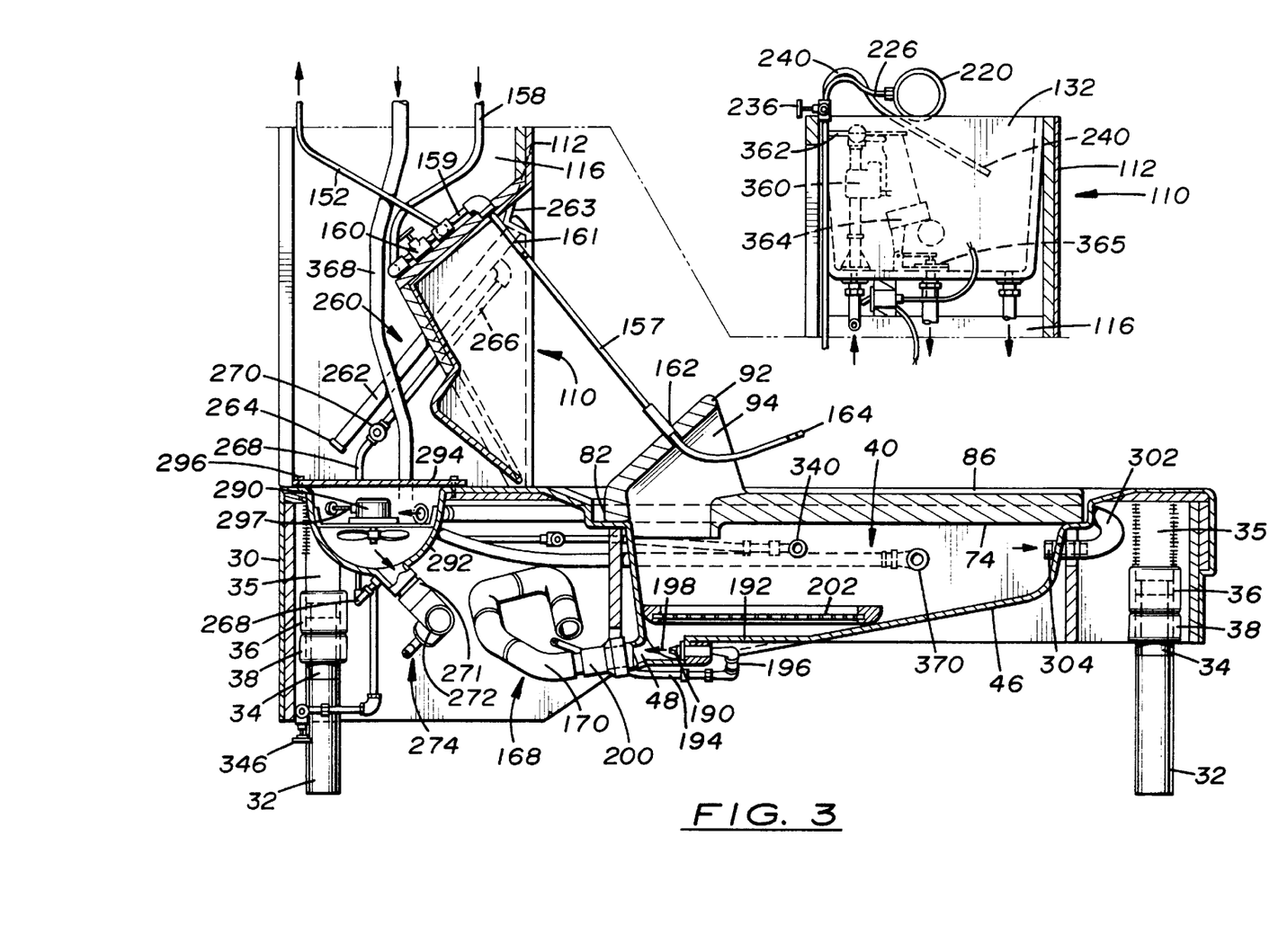
FIG. 3, a longitudinal vertical section view taken on the line 3—3 of FIG. 5.
Figure 4:
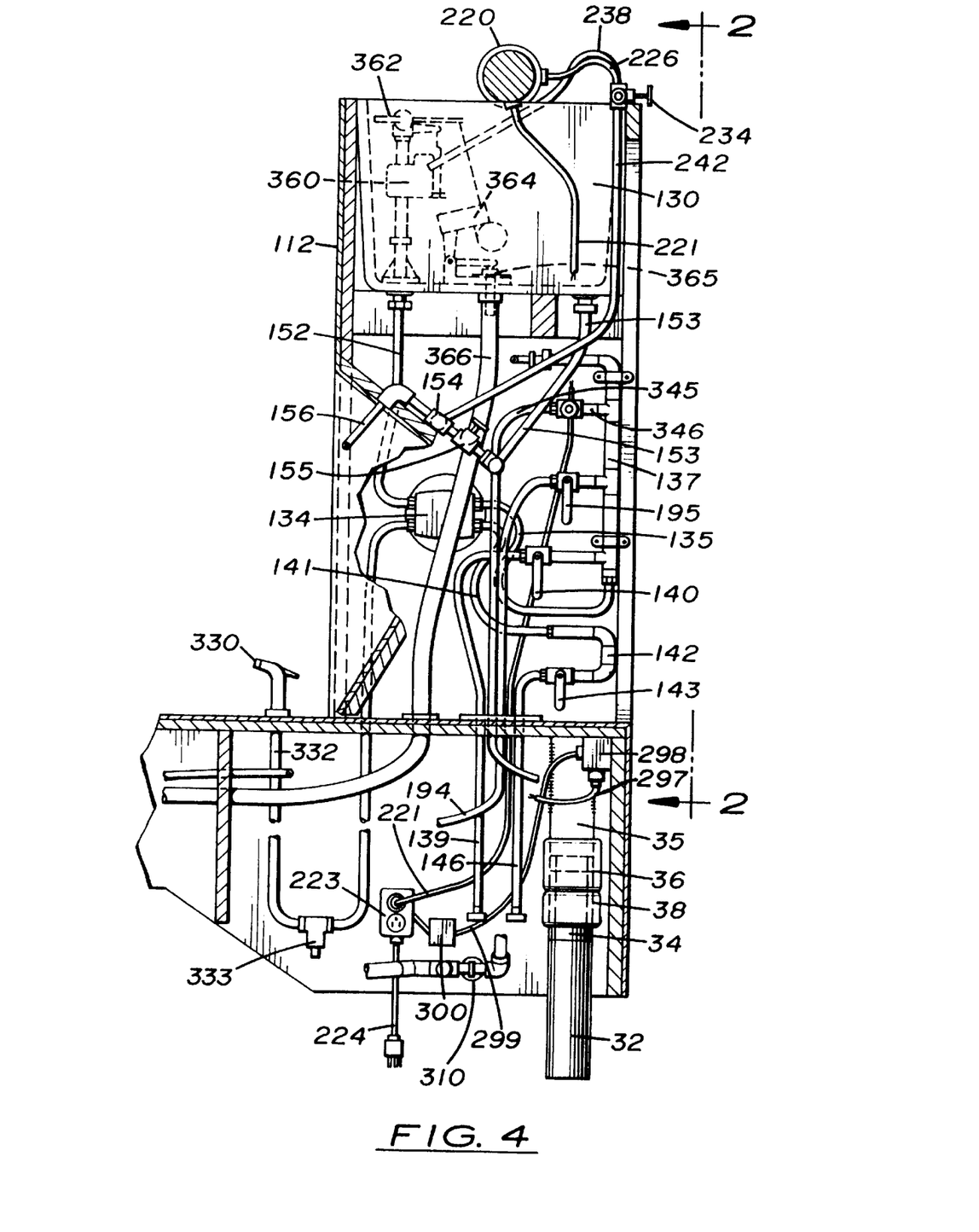
FIG. 4, a fragmentary longitudinal section view taken on the line 4—4 of FIG. 5.
Figure 5:
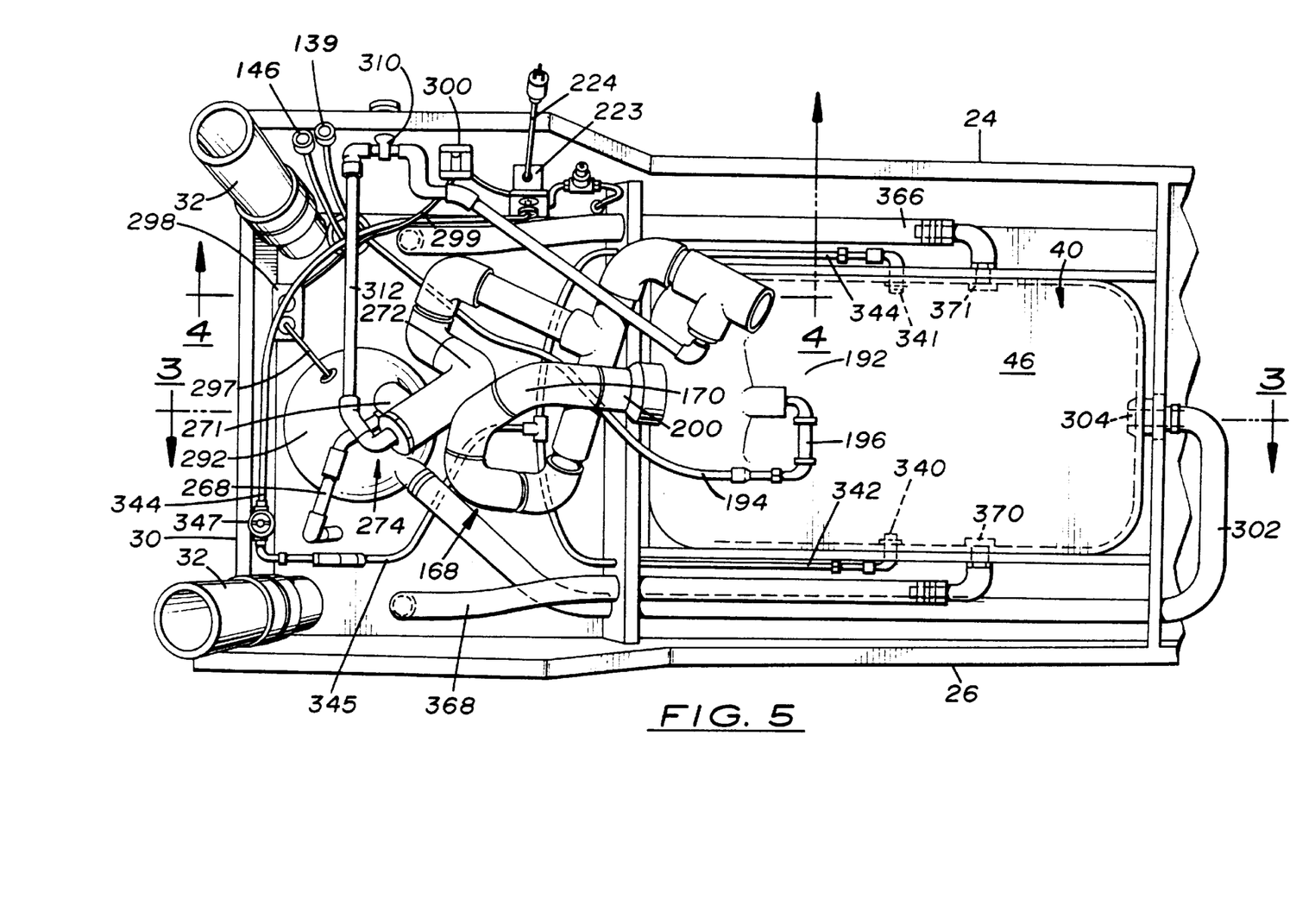
FIG. 5, a bottom plan view of the invention.

The colon cleansing apparatus support structure further includes a cabinet 110 having a front panel 112, a right side panel 114, and a left side panel 116. Cabinet 110 may be constructed from wood covered with an appropriate medical grade coating or from metal such as stainless steel or aluminum. Cabinet 110 rests on the end of table top surface 22 and is removably held thereto by means of a plurality of bolts 118 which extend through the lower part of side panels 114 and 116 threading into the respective table side panel 24 and 26.

Figure 6:
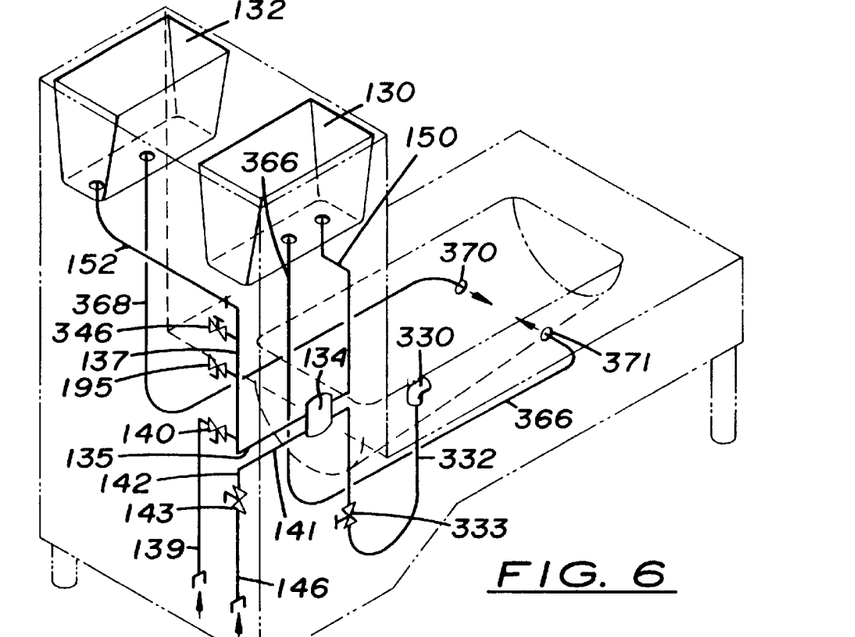
FIG. 6, a schematic diagram of the hand sprayer system and the warm and cold water flushing system of the invention.
Figure 6A:
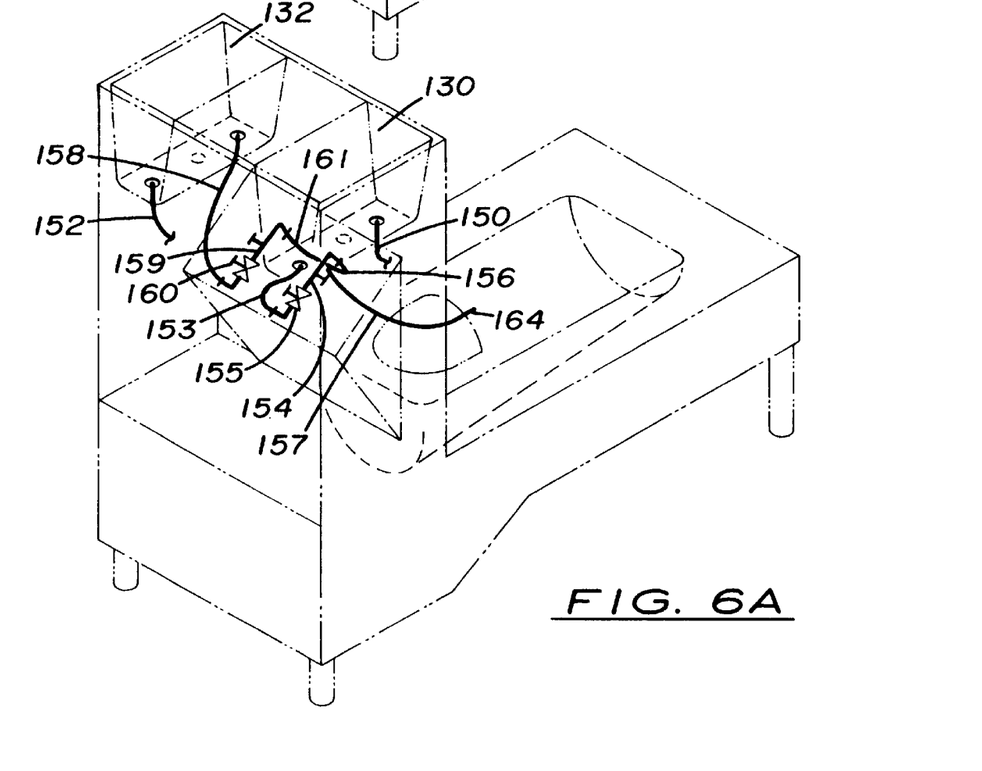
FIG. 6A, a schematic diagram of the warm and cold water introduction system.

A fluid delivery means comprises a warm and cold water introduction system through which water is fed to the colon irrigation unit 52 for entry through the rectum into a person's colon comprises a warm water tank 130 and a cold water tank 132 attached to the upper end of cabinet 110. Warm water is introduced into warm water tank 130 by means of a blending means comprising a tempering valve 134 connected to cold water by means of a hose 135 attached to a cold water common pipe 137. Cold water common pipe 137 receives cold water from a standard cold water supply pipe (not shown) by means of a hose 139 with a manually actuated valve 140 interposed therebetween. Tempering valve 134 receives hot water to mix with the cold water by means of a hose 141 connected to a hot water common pipe 142 with the water flow regulated by means of a manually actuated valve 143 connected to hot water common pipe 142. Hot water common pipe 142 receives hot water from a standard hot water supply pipe (not shown) by means of a hose 146 connected to manually actuated valve 143.

Tempering valve 134 can be set to a desired warm water temperature for introduction into warm water tank 130 by means of a built in thermostat manually set by a dial 148, typically set between about seventy and one hundred and ten degrees Fahrenheit so as not to scald a person, and which automatically blends the hot and cold water to attain the set temperature. Tempering valve 134 has an anti-scald means built-in such that scalding water cannot be passed through to warm water tank 130. The warm water from tempering valve 134 is fed to warm water tank 130 by means of a hose 150. Cold water is directly fed from cold water common pipe 137 through a manually actuated valve 151 through a hose 152 to cold water tank 132. Warm water from warm water tank 130 is fed through a hose 153 to a pipe 154 having a manually actuated valve 155 for warm water flow control which is attached to a tube 156 extending through cabinet front 112 into a main tube 157. Cold water from cold water tank 132 is fed through a hose 158 to a pipe 159 having a manually actuated valve 160 for cold water flow control which is attached to a tube 161 extending through cabinet front panel 112 into main tube 157. Main tube 157 leads to colon irrigation unit 52 and extends through an aperture 162 through shield 94 of colon irrigation unit 52. Disposable tip 164 fits in the end of main water tube 156 which tip is inserted in the person's rectum for entry of water into the person's colon. Expelled water and fecal matter exit through the person's rectum and are directed through colon irrigation unit opening 94 into basin drain 48 which leads into a standard sewer pipe (not shown) by means of a pipe 168 having a trap means comprising a trap 170 in which water pools so as to prevent odors from emanating from the sewer pipe back into the basin 40.

Figure 8:
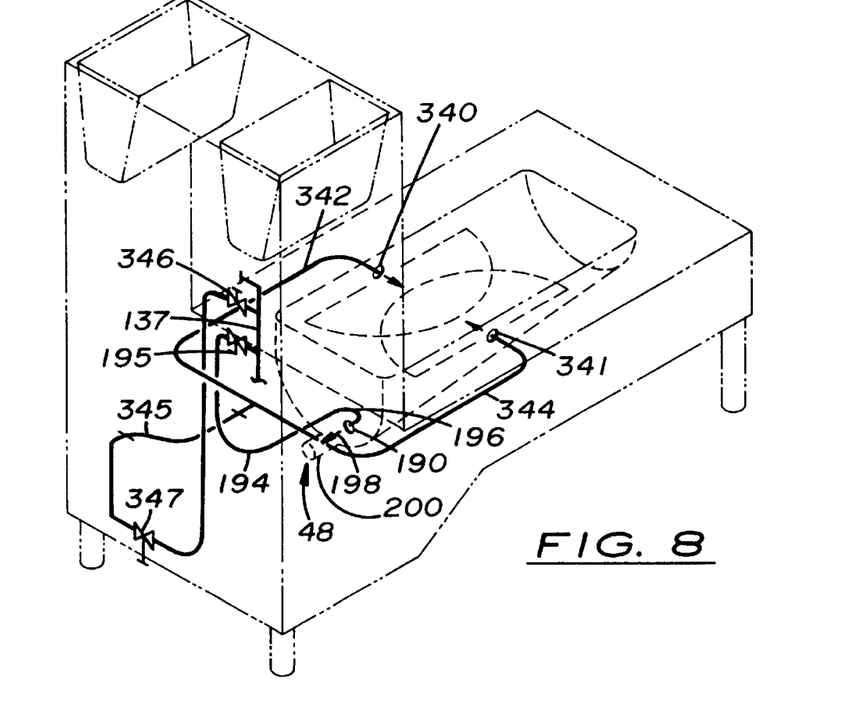
FIG. 8, a schematic diagram showing the fan spray washing system and the pressure spraying system of the invention.

A pressure spray means comprises a pressure spray system aids in keeping the drainage means leading from drain opening 48 to the sewer pipe from clogging with fecal and other matter. The system comprises a power spray nozzle 190 which is affixed to a humped portion 192 of basin 40. Power spray nozzle 190 is fed cold water from cold water common pipe 137, through a hose 194 having a manually actuated valve 195 to adjust the flow of water therethrough, and through a pipe 196. The concentrated, focused pressure water spray 198 from power spray nozzle 190 is directed generally horizontally into drain 48 which is directly connected to a about two inch long short section 200 of pipe 168, both drain 48 and short section 200 being of which are of a smaller diameter than the rest of pipe 168 and the sewer pipe such that any fecal matter small enough to pass through drain 48 and short section 200 will not go into pipe 168 nor the sewer pipe enabling easy access thereto. Also, pieces of fecal matter initially too large to pass through drain 48 and short section 200 are broken into smaller pieces by water spray 198 such that they can pass through drain 48 and short section 200. A removable screen 202 may be positioned at the bottom of the basin 40 to catch the larger debris which a doctor may find of interest including parasites, undigested pills, etc. An upwardly curved section of 203 may be used in conjunction with power spray nozzle 190 to force fecal and other matter away from basin 40.

Figure 9:
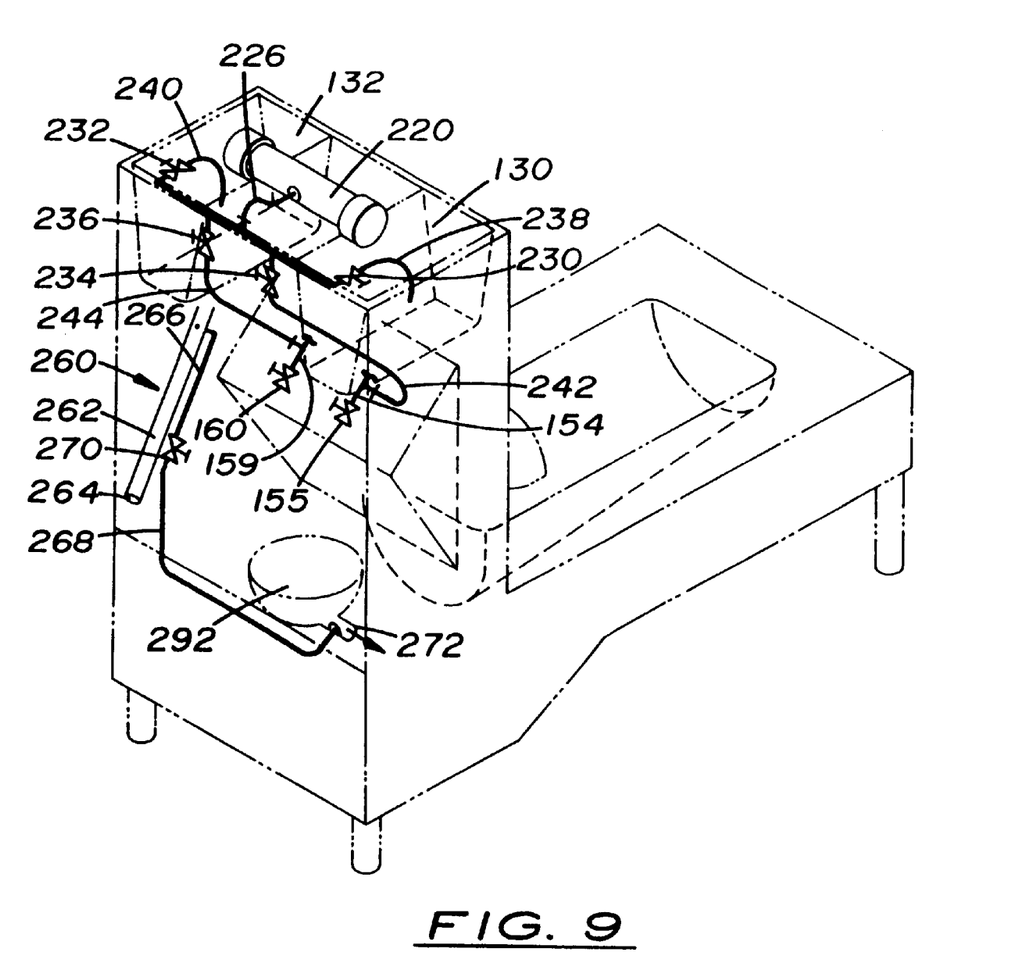
FIG. 9, a schematic diagram showing the ozone with sterilization chamber system of the invention.

An ozone generating and delivery means comprising an ozone system allows the introduction of ozone into the water for sterilization purposes to kill micro-organisms and for therapeutic use upon a doctors prescription and supervision. The system comprises a standard type electrical ozone generator 220 mounted to the upper portion of cabinet 110 above warm and cold water tanks 130 and 132. Ozone generator 220 has an electrical cord 221 with a manually actuated electric switch 222 interposed therein which leads to a main power outlet 223. Main power outlet 223 receives electrical current through a power cord 224 which plugs into a standard power outlet (not shown). A tube 226 extends from ozone generator 220 which conveys ozone to a four-way manually actuated gang valve 228 having individual valves 230, 232, 234, and 236. Connected to valve 230 is a hose 238 which leads to the bottom portion of warm water tank 130 and connected to valve 232 is a hose 240 which leads to the bottom portion of cold water tank 132. By opening valves 230 and 232 ozone is bubbled through the water in warm water tank 130 and through the water in cold water tank 132, respectively, which sterilizes the water therein but also sterilizes the respective tanks 130 and 132. Connected to valve 234 is a hose 242 which connects with warm water pipe 154 and connected to valve 236 is a hose 244 which connects with cold water pipe 159. By opening valve 234 and 236 ozone is mixed with the warm and cold water flowing through tubes 152 and 158, respectively, into main tube 157. The ozone sterilizes pipes 153 and 159, tubes 155, 161, and main tube 157. The introduction of small amounts of ozonated water into the colon is said to kill pathogens and parasites therein and may be done but only under a doctor's prescription and supervision.

The ozone system has a sterilization chamber 260 which is used to sterilize the end portion of main tube 157 after removal of disposable tip 164. Sterilization chamber 260 has a tubular body 262 mounted to cabinet front panel 112 by means of a bracket 263 and extends downwardly through a front panel 112 at an angle thereto and which terminates in a water tight cap 264. Sterilization chamber 260 has an overflow tube 266 attached to the upper end of tubular body 262 and which extends generally parallel thereto. The other end of overflow tube 266 is connected to a pipe 268 having a manually actuated valve 270 and which connects to a pipe 271 which connects with a pipe 272 having a trap means comprising a trap 274 therein where water pools and which connects to pipe 168 to the sewer pipe. Sterilization chamber 260 is operated by removing disposable tip 164 from the end of main tube 157 and inserting the end of main tube 157 into sterilization chamber tubular body 262. Tubular body 262 and overflow tube 266 is then filled with water by manually opening valve 154 and valve 160 to allow water into and through main tube 157 into tubular body 262 and overflow tube 266. Valves 234 and 236 are then manually opened and electrical switch 222 turned on to start ozone generator 220 producing ozone. Ozone bubbles out of the end of main tube 157 along the length thereof in tubular body 262 along the outside so as to sterilize outside as well as the inside surfaces of main tube 157.

Figure 7:
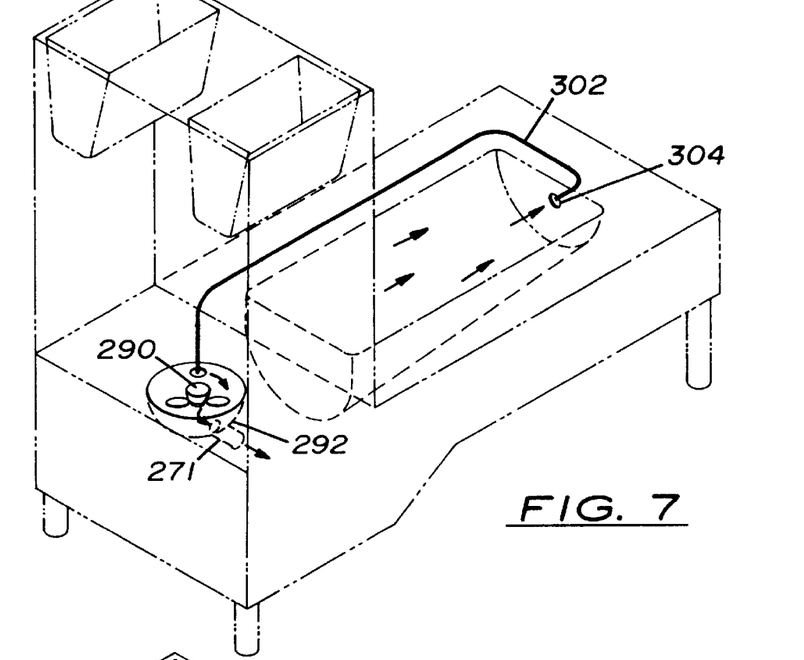
FIG. 7, a schematic diagram showing the odor exhausting system of the invention.

An odor exhausting means comprises an odor exhausting system which is used to remove the odor emitted by the expelled water and fecal matter. The system comprises an electric fan 290 mounted within a bowl-shaped fan chamber 292 in the upper surface 22 of table 20 under cabinet 110. Fan 290 is located at a vertical height so as not be in danger of becoming wet. A circular removable fan chamber cover 294 is disposed at the top of fan chamber 292 so as to completely enclose fan chamber 292 and is secured by screws 296. Fan 290 is connected by means of an electrical cord 297 to an electrical box 298 which is connected to main power outlet 223 by means of a power cord 299 with a manually actuated electrical switch 300 inter-posed therebetween to turn on and off fan 290. A hose 302 leads from an air inlet 304 through front wall 42 of basin 40 at a position above the water line (not shown) thereof into fan chamber 292 below fan chamber cover 294. Fan chamber 292 connects with pipe 271 to pipe 272 with trap 274 and connects to pipe 168 leading to the sewer pipe such that when fan 290 is turned on by means of switch 300 odors are drawn from within basin 40 through air inlet 304, hose 302, fan chamber 292, pipe 271, pipe 272 with trap 274, pipe 168 and into the sewer pipe. Trap 274 in pipe 272 prevents odors from emanating from the sewer pipe backwards into basin 40. Water enters trap 274 by means overflow from sterilizing chamber 260 flowing into overflow tube 266, through pipe 268 with manually actuated valve 270, pipe 271, and into pipe 272 with trap 274. A drain pipe 308 having a valve 310 leads from the bottom of trap 274 into pipe 168 connected to the sewer pipe. When fan 290 is not being used valve 310 is closed and the overflow from sterilization chamber 260 fills trap 274 which prevents odors from emanating from the sewer pipe. Just before fan 290 is to be turned on by means of manually actuated electric switch 300 manually actuated valve 310 is opened so as to allow the water in trap 274 to drain such that air can pass through trap 274 and into the sewer pipe.

After colon cleansing is completed a hand held sprayer system allows any fecal or other matter on the user to be cleaned off and washed into basin 40 and down drain 48. Likewise, any fecal or other matter in basin 40 on other parts of the apparatus may be washed down basin drain 48. The sprayer system comprises a hand actuated valved sprayer head 330 which has a tube 332 attached thereto which extends from tempering valve 134 through table top surface 22 with a pressure regulator 333 therebetween. Tempering valve 134 assures that the water emitted from sprayer head 330 is at the same preset temperature as the water in warm water tank 130 so as not to scald a person using the sprayer system and at a lower, usable pressure. In a retracted position tube 332 fully stows under table top surface 22 with sprayer head 330 adjacent thereto. In an extended position tube 332 extends therefrom to reach the desired area to be cleaned.

Cleaning of the basin 40 and of the lower wall 74 of colon irrigation unit 52 can be done by fan spray means comprising a fan spray washing system which includes a pair of fan spray nozzles 340 positioned at opposite sides of basin 40 through bottom wall 46 above the water line intermediate front and rear walls 42 and 44. A pair of hoses 342 and 344 lead from respective fan spray nozzles 340 and 341 to cold water common pipe 137 with a hand actuated valve 346 interposed therebetween. Fan spray nozzles 340 spray a fan-shaped spray the pair of which contact all of basin 40 and the bottom surface 74 of colon irrigation unit 52 such that fecal and other matter thereon is directed through drain 48.

A flush means comprises a warm and cold water flushing system can be used to introduce a large volume of water such as about three gallons to 20 or more similar to that amount flushed in a standard toilet into basin 40 which is particularly useful to flush large quantities of fecal and other matter down drain 48. The system comprises a standard hand activated flush-type valve 360 having a flush handle 362, filling means comprising a float valve 364 to fill up the tank, and a flopper valve disposed in each of warm and cold water tanks 130 and 132 which flopper valves are each connected to large diameter pipes 366 and 368, respectively, leading into basin 40 at opposite sides thereof. Either or both of warm and cold water tanks 130 and 132 can be flushed into basin 40 depending on the volume of water needed to flush basin 40.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A colon cleansing apparatus for connection to hot and cold water supply pipes and to a sewer pipe, the apparatus used in conjunction with a colon cleansing unit of the type having an conjunction with a colon cleansing unit of the type having an elongate support surface with an outlet opening therein, comprising:
 a support structure having basin with a drain outlet therein and adapted to support the colon cleansing unit above said basin;
 a water tank supported by said support structure at a vertical height above said basin and the cleansing unit;
 filling means adapted to be connected to a water supply pipe and to said tank and adapted for filling said tank with water;
 delivery means adapted to allow selective movement of water from said water tank to the colon cleansing unit for introduction through the rectum into the colon of a person to dislodge matter therein, which water with dislodged matter is expelled from the rectum into the opening in the colon irrigation unit into said basin; and
 drainage means connected to said basin at said drain and adapted to connect to the sewer pipe for moving the expelled water and matter from said basin into the sewer pipe.

2. A colon cleansing apparatus according to claim 1, wherein the filling means automatically refills the water tank to a predetermined level upon draining of any water therefrom.

3. A colon cleansing apparatus according to claim 1, wherein the filling means is adapted to be connected to both the hot and cold water supply pipes and further comprises thermostatically controlled blending means for mixing the water from the hot and cold water supply pipes to deliver water to the water tank at a predetermined temperature.

4. A colon cleansing apparatus according to claim 3, further comprising:
 a second water tank;
 wherein the filling means is adapted to fill said second tank with cold water; and
 the delivery means is adapted to allow selective movement of water from one or both of said tanks to the colon cleansing unit for introduction through the rectum into the colon of a person.

5. A colon cleansing apparatus according to claim 4, further comprising flushing means connected to each of the water tanks and adapted to allow selective rapid draining of one or both tanks into the basin.

6. A colon cleansing apparatus according to claim 3, wherein the blending means prevents scalding water from being delivered to the tank for introduction into the colon of a person.

7. A colon cleansing apparatus according to claim 6, wherein the blending means is a tempering valve.

8. A colon cleansing apparatus according to claim 1, further comprising ozone generating and delivery means adapted to generate and deliver ozone into the water contained in the tank for sterilization of said tank and the water contained therein.

9. A colon cleansing apparatus according to claim 1, further comprising ozone generating and delivery means adapted to generate and deliver ozone into the water delivery means for sterilization thereof.

10. A colon cleansing apparatus according to claim 9, wherein:
 the delivery means includes a tube which transports the water to the colon irrigation unit with a free end thereat; and
 the ozone generating and delivery means includes a sterilization chamber into which said free end of said tube can be inserted therein and water with ozone bubbled through and around the outside of said free end to sterilize said free end.

11. A colon cleansing apparatus according to claim 1, further including a fan spray means for delivering water from the cold water supply pipe and having a pair of nozzles spraying the water from opposing sides of the basin each in a fan-shaped pattern so as to substantially spray clean said basin and a bottom surface of the colon irrigation unit.

12. A colon cleansing apparatus according to claim 1, wherein:
 the drainage means includes a piping means which leads from the drain opening of the basin to the sewer pipe, with said drain opening and a short section of said piping means connected thereto having a smaller cross-sectional area than the remainder of said piping means and the sewer pipe; and
 a pressure spray means adapted to connect to the cold water supply pipe to channel water to a nozzle thereof directed at said drain of said basin so as to break up pieces of fecal and other matter too large to fit through said drain opening and said short section into smaller pieces which can pass therethrough.

13. A colon cleansing apparatus according to claim 1, further comprising flushing means connected to the water tank and adapted to allow selective rapid draining of said tank into the basin.

14. A colon cleansing apparatus according to claim 1, further comprising odor exhausting means having a fan which can be selectively turned on and off operatively connected to the basin and to the sewer pipe for exhausting air containing odors from said basin.

15. A colon cleansing apparatus according to claim 14, wherein the odor exhausting means includes trap means which can be selectively filled water and drained of water so as to be drained when said fan is turned on so as to let air pass therethrough and subsequently filled with water when said fan is turned off so as to prohibit odors from exiting from the sewer pipe.

16. A colon cleansing apparatus according to claim 1, wherein the drainage means includes trap means which fills with water drained thereinto so as to prohibit odors from exiting from the sewer pipe into the basin.

17. A method of cleaning and sterilizing a colon cleansing apparatus of the type having a water delivery means including a tube having a free end for delivering water from a water source through a person's rectum into their colon, the apparatus for use with a separate colon irrigation unit including bottom and an opening through the bottom which water and matter expelled from the person's rectum passes, the apparatus further having a basin positioned below the colon cleansing unit to catch the water and matter and direct it through a drain opening on the basin into a drainage means connected to a sewer pipe, comprising the steps of:
 inserting the free end of the tube into a sterilization chamber of the apparatus;
 running water through the hose; and
 adding ozone from an ozone generator of the apparatus to the water running through the hose into said sterilization chamber and around the outside of the free end so as to sterilize the free end.

18. A method according to claim 17, further comprising the step of rinsing the basin and the bottom of the colon irrigation unit comprising the step of spraying a generally horizontally fan-shaped spray of water from opposite sides of the basin by means of a fan spray system of the apparatus.

19. A method according to claim 17, further comprising the step of breaking up large pieces of expelled matter by spraying a concentrated spray of water at the drain and pieces of matter too large to go down the drain opening and a short section of pipe connected thereto of said drainage system, wherein the drain opening is generally vertically oriented and the short section of pipe and the drain opening are of a smaller cross-sectional area than the remainder of a pipe of the drainage means connected to the sewer pipe.

20. A method according to claim 17, further comprising the step of rinsing the basin by flushing a large volume of water into the basin and down the drain by using a quick flushing system of the apparatus.

21. A method according to claim 17, further comprising the step of removing odors from the basin by turning on an electric fan means which draws air containing odors from the basin, conveys the air with odors into the sewer pipe, and which blocks the return of the air with odors from returning to the basin upon turning off the fan means by trap means therein.

* * * * *